United States Patent [19]

Pez et al.

[11]  4,356,337
[45]  Oct. 26, 1982

[54] PRODUCING CYCLOHEXENE OR ALKYLCYCLOHEXENE

[75] Inventors: Guido P. Pez, Boonton; Irving L. Mador, Morristown, both of N.J.

[73] Assignee: Allied Corporation, Morris Township, Morris County, N.J.

[21] Appl. No.: 317,626

[22] Filed: Nov. 2, 1981

[51] Int. Cl.³ .............................................. C07C 5/00
[52] U.S. Cl. .................................. 585/267; 585/266; 585/350; 585/500
[58] Field of Search ................................ 585/267, 266

[56] References Cited

U.S. PATENT DOCUMENTS 2,960,544  11/1960  Mador et al. ........................ 260/665

OTHER PUBLICATIONS

A. J. Birch et al., *Quarterly Reviews*, pp. 17–33, (1958).
K. Tamaru, *Catalyst Reviews*, vol. 4, No. 2, pp. 161–178, (1970).
Bank et al., *J. Am. Chem. Soc.*, vol. 90, pp. 4505–4506, (Jul. 31, 1968).
E. Grovenstern, *NTIS Publication*, PB-220 572, (1973).
R. G. Kooser et al., *J. Chem. Phys.*, vol. 50, 5243, (1969).

*Primary Examiner*—Delbert E. Gantz
*Assistant Examiner*—Asokkumar Pal
*Attorney, Agent, or Firm*—Alan M. Doernberg; Gerhard H. Fuchs

[57] ABSTRACT

Benzene or an alkylbenzene is reacted with hydrogen and an alkali metal such as potassium in the presence of a polyamine to produce cyclohexene or alkylcyclohexene and alkali metal hydride. The polyamine contains only C, N and H and has at least three nitrogens. Each nitrogen is linked to three carbons and each carbon bridge is at least two methylenes long. Representative polyamines are hexamethyl hexacyclen, hexamethyl triethylene tetraamine, tris(2-dimethylamino ethyl)amine and octamethyl pentaethylene hexamine. Cyclohexene is produced at high ratios with respect to cyclohexane.

10 Claims, No Drawings

PRODUCING CYCLOHEXENE OR ALKYLCYCLOHEXENE

BACKGROUND OF THE INVENTION

The present invention relates to the selective hydrogenation of benzene and alkyl-substituted benzenes, by hydrogen and an alkali metal to produce cyclohexene and alkylcyclohexenes and alkali metal hydride by-product.

The Birch Reaction, disclosed for example by A. J. Birch et al. in *Quarterly Reviews*, pp. 17–33 (1958) involves the reduction of aromatics by an alkali metal and an alkanol in ammonia. See especially pages 17–20. At page 20, lithium in monoamines of low molecular weight is indicated as a powerful reducing agent with little selectivity.

K. Tamaru, *Catalyst Reviews*, vol. 4, number 2, pages 161–78 (1970) indicates that sodium reacts with anthracene to form a disodium dianthracene complex, which might react further with hydrogen to form 9,10-dihydroanthracene and sodium hydride. See pages 164–166.

Bank et al., *J. Am. Chem. Soc.*, volume 90, pages 4505–06 (July, 31, 1968) reports that sodium and hydrogen react in naphthalene and tetrahydrofuran to give sodium hydride and no hydrogenated naphthalenes (to the detection limits of about 0.2%).

E. Grovenstern, in NTIS Publication, PB-220 572 (1973) indicates that cesium reacts with benzene to give a black precipitate, whereas benzene fails to react with sodium-potassium alloy to give appreciable quantities of radical anion (citing R. G. Kooser et al., J. Chem. Phys., volume 50, 5243 (1969)). The cesium precipitate reacted with water to give a mixture of products including hexadiene.

U.S. Pat. No. 2,960,544 to Mador and Soddy (1960) discloses the reaction of an alkali metal such as potassium with benzene or an alkylbenzene in the presence of certain ethers or tertiary monoamines to form adducts which can be further reacted in Grignard-type reactions. No hydrogenation is disclosed.

BRIEF DESCRIPTION OF THE INVENTION

The present invention includes the process for the selective hydrogenation of aromatic hydrocarbons which comprises reacting a liquid aromatic hydrocarbon selected from the group consisting of benzene and alkylbenzenes containing 7–10 carbons with an alkali metal selected from the group consisting of sodium, potassium and mixtures thereof, and with hydrogen in the presence of a polyamine containing only C, N and H, with at least 3 nitrogens, each nitrogen being linked to three carbons and each carbon bridge between nitrogens being at least two methylene units long, under conditions producing cyclohexene or alkylcyclohexene and a hydride of said alkali metal. High selectivity to cyclohexene and alkylcyclohexene is observed.

DETAILED DESCRIPTION OF THE INVENTION

The present invention relates to processes for selectivity hydrogenating benzene or alkylbenzenes to cyclohexene or alkylcyclohexenes. The Applicants believe, without limiting the present invention to any theory, that the tertiary polyamine stabilizes the sodium and/or potassium counterions of the aryl (e.g. benzene) radical anion in a manner that permits its reaction with dihydrogen to form a first product (e.g. cyclohexadiene) with agains reacts with alkali metal to form a radical anion and a counterion. The cyclohexadiene is not actually seen as a reaction product. It is expected to react rapidly, as the radical anion, with dihydrogen to yield cyclohexene, which is substantially inert to further reaction with alkali metal.

Alkali metals useful in the present invention are sodium, potassium and mixtures thereof. While pure potassium is most active, mixtures are also preferred because of the lower cost of sodium. Two representative mixture are 78 weight % K - 22% Na and sodium with a minor amount (e.g. 5) potassium. Sodium by itself was inactive for benzene as the aromatic in the apparatus employed, but may have some activity with sufficient agitation or with alkylbenzenes.

The aromatic hydrocarbon used is benzene itself or alkylbenzenes such as toluene, ethylbenzene, propylbenzene or cumene.

In general, it is preferred to use amounts of alkali metal at or in excess of the stoichiometric level relative to aromatic hydrocarbon and to use hydrogen in excess. The stoichiometric mole ratio of benzene to potassium to dihydrogen is 1:4:4, based upon the equation:

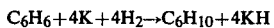

$$C_6H_6 + 4K + 4H_2 \rightarrow C_6H_{10} + 4KH$$

The polyamine used in the present invention need be present only in catalytic amounts. It contains at least three nitrogens, has each nitrogen linked to three carbons (i.e. tertiary) and has carbon bridges between nitrogens at least two carbons long. Carbon bridges only one methylene unit long have hydrogens which are too acidic for the present invention. Preferred polyamines are those with ethylene bridges between carbons and methyl or ethyl as the remaining substituents on the nitrogens.

Suitable polyamines include linear polyamines with alkylene bridges (preferably ethylene) between nitrogens and two alkyls on each end nitrogen and one alkyl on each intermediate nitrogen. Preferred here are polyamines of the formula:

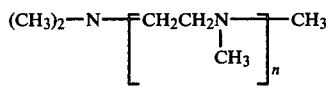

with n being between 3 and 6. In Example 2, such an amine with n=3 are used; in Example 7 such as amine with n=5 was used. Another preferred group of polyamines are branched polyamines with at least one nitrogen linked by three alkylenes of at least two carbon to three other nitrogens. The simplest of these is N[CH$_2$CH$_2$N(CH$_3$)$_2$]$_3$. Based upon the limitation of each N being tertiary and each bridging group having at least two methylenes, other suitable branched polyamines can be determined. A third group of suitable polyamines are the circular or "crown" polyamines with tertiary nitrogens linked in a circular fashion by alkylenes. These are described in some detail in commonly assigned, copending application Ser. No. 317,627, (filed herewith) of J. Galle and have, in the simplest case, a formula such as

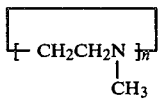

where n is between 5 and 8. Known crown compounds such as hexacyclen

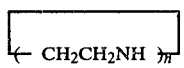

are themselves unsuitable because of the H bonded to N, but they may be converted to suitable polyamines by methylation, with suitable methylation reagents including formaldehyde/formic acid. While the cyclic polyamines generally gave the best reaction rates, they were generally more susceptible to decomposition by the alkali metal than the linear or branched polyamines.

Reaction temperature was not found to be especially critical, with room temperature appearing to be near optimal. Hydrogen pressure should be superatmospheric, and is preferably at least 5 atmospheres (0.5 MPa). As in other reactions of alkali metals, vigorous agitation and especially high shear rates are preferred. While continuous reaction is possible, it is generally preferred to conduct the reaction on a batch basis, and then separate reactants and products by evaporation and distillation. The alkali metal hydride can then be separated from the polyamine solution by conventional solid/liquid separation techniques (e.g. centrifugation, filtration). Solvents beyond the aromatic hydrocarbon reactants are not required, but may be used if sufficiently inert.

EXAMPLES

All of the chemicals used were of the highest purity available and were handled with the rigid exclusion of oxygen and moisture. A Vacuum Atmospheres drybox, filled with argon gas, containing <5 ppm $O_2$ or $H_2O$, was used for the transfer and handling of the amines, solids and Na/K alloy. The solvents were purified by treatment with Na/K alloy under $N_2$ and were transferred using standard vacuum line techniques. Some of the amines were purified as indicated in Examples 11 and 12.

Reactions were carried out on a stainless steel pressure/vacuum line up to 1034 kPa, using a heavy wall glass pressure tube fitted with an 8-mm Kontes high vacuum teflon stopcock to which a ⅜ inch (9.5mm) outside diameter tube was attached. The tube was connected to the metal line using a Swagelok nut and Teflon ferrules. For pressures above 1034 kPa, a 35 mL stainless steel Parr bomb was used.

A Hewlett Packard gas chromatograph, model 5830 was used for analysis. Good separation between cyclohexane, cyclohexene and benzene was achieved using a 15 feet (4.57 m) long, one-eight inch (3.2 mm) diameter stainless steel column packed with 10% tris(cyanoethoxy) propane (TCEP) on 80/100 Chromosorb P AW (Supelco #1-2122). This column was also used to analyze toluene and its hydrogenation products. A column of the same diameter, but one-third the length packed with 10% Apiezon L, 2% KOH on 80/100 Chromosorb W AW (Supelco #1-1893) was used for the amine analyses.

EXAMPLE 1

A 35 mL heavy wall glass pressure tube, containing a Pyrex covered magnetic stir bar, was charged (in the drybox) with about 1.5 grams of Na/K alloy (75 wt. % K), and hexamethyl hexacyclen (HMH) (232 mg, 0.677 mmol). The reactor was then connected to a stainless steel pressure/vacuum line and evacuated ($10^{-5}$ torr). Stirring the amine+Na/K at room temperature (25° C.) produced a dark blue color. The reactor was then immersed in liquid $N_2$ and benzene (460 mg, 5.89 mmol) was distilled into it. The apparatus was slowly warmed to room temperature with stirring. The blue amine+alloy mixture turned dark blue-black immediately upon contact with the benzene. This was stirred at room temperature for about 5 minutes after which time the apparatus was pressurized with 1020 kPa $H_2$ (Matheson UHP). After 3-4 hours reaction time, the blue solution was decolorized to brown. A reaction time of 19 hours produced a white slurry. The volatile liquids were collected in an in-line trap cooled to −196° C., and analyzed by gas chromatography. Found: 0.08% cyclohexane, 44.95% cyclohexene and 54.95% benzene. % Benzene Conversion =45.03, % Selectivity (with respect to cyclohexene as a percentage of cyclohexene plus cyclohexane) =99.8.

Fresh benzene (337 mg, 4.31 mmol) was distilled into the reactor. The thick white slurry was stirred for several minutes at 25° C., then the apparatus was repressurized with 965 kPa $H_2$. After 17 hours reaction time, the volatile liquids were collected as described above and analyzed by gas chromatography. Found: 0.00% cyclohexane, 6.09% cyclohexene and 93.87% benzene. % Conversion=6.09, % Selectivity=100.00.

Gas chromatography analysis of the contents of the pressure tube showed extensive decomposition of the hexamethyl hexacyclen. The decomposition products could not be identified.

EXAMPLE 2

A 35 mL heavy wall glass pressure tube was charged with a 22/78 (by weight) Na/K alloy (131.3 mg), hexamethyl triethylene tetramine (HMTT) (250.4 mg, 1.086 mmol) and benzene (625 mg, 8.01 mmol) as in Example 1. Stirring the clear reactants at 25° C. for 0.5 hour produced a yellow color. The apparatus was then pressurized with 841 kPa $H_2$, which caused the yellow solution to immediately turn green. A gray slurry was evident after reacting for 18 hours. After 40 hours, it appeared to be more viscous. The apparatus was cooled to −196° C. and the $H_2$ was pumped off. The liquids were decanted into the side arm of the reactor which was capped with a rubber septum. The samples were taken directly from the side arm and analyzed by G.C. Found: 0.00% cyclohexane, 9.88% cyclohexene and 90.11% benzene. % Conversion=9.88, % Selectivity=100.00. Virtually all of the HMTT (98%) was recovered (as determined by quantitative G.C. analysis) and the chromatogram showed no evidence of decomposition products.

EXAMPLE 3

A 35 mL heavy wall glass pressure tube was charged with a 22/78 (by weight) Na/K alloy (171 mg), tris(2-dimethyl amino ethyl)amine (iso-HMTT) (217 mg, 0.94 mmol) and benzene (887 mg, 11.36 mmol) as in Example 1. A bright yellow color was produced after the clear reaction mixture was stirred for 20 minutes at 25° C.

When the apparatus was pressurized with 979 kPa $H_2$, the color changed to yellow-green. A yellow-green slurry was evident after reacting for 3 hours. Further reaction (21 hours total) produced a gray slurry. The apparatus was cooled to −196° C. and the $H_2$ was removed by pumping. The volatile liquids were distilled into a received and analyzed by G.C. Found: 0.00% cyclohexane, 4.95% cyclohexene, 4.95% cyclohexene and 94.94% benzene. % Conversion=4.95, % Selectivity =100.00. Analysis of the recovered iso-HMTT (96%) showed no evidence of degradation.

EXAMPLE 4

A 35 mL stainless steel Parr bomb was charged with a 22/78 (by weight) Na/K alloy (1500 mg), iso-HMTT (300 mg, 1.3 mmol) and benzene (893 mg, 11.4 mmol) as in Example 3. The reactants were stirred for 5 minutes at 25° C., under vacuum, after which time the apparatus was pressurized with 6895 kPa $H_2$. The reaction was stirred overnight for a total of 20 hours. The volatile liquids were collected in an in-line trap (−196° C.) and analyzed by gas chromatography. Found: 0.42% cyclohexane, 10.59% cyclohexene and 88.98% benzene. % Conversion=11.01, % Selectivity=96.19. Gas chromatography analysis of the recovered amine showed no evidence of degradation.

EXAMPLE 5

A 35 mL heavy wall glass pressure tube was charged with 22/78 Na/K alloy (194.5 mg), iso-HMTT (332 mg, 1.44 mmol) and benzene (897 mg, 11.48 mmol). The reaction was charged and run in the same manner as Example 3 except that the pressure tube was stirred in an ultrasonic bath filled with silicone oil. The volatile liquids were collected in an in-line trap and analyzed by gas chromatography. Found: 0.00% cyclohexane, 6.75% cyclohexene and 93.25% benzene. % Conversion=6.75, % Selectivity=100.00. G.C. analysis of the recovered amine (96%) showed no evidence of degradation.

EXAMPLE 6

A 35 mL stainless steel Parr Bomb was charged with Na/K alloy (640 mg), iso-HMTT (330 mg, 1.43 mmol) and benzene (1089 mg, 13.95 mmol) as in Example 5. The reaction was stirred for 18 hours under 5488 kPa $H_2$. the volatile liquids were collected in an in-line trap (−196° C.) and analyzed by G.C. Found: 1.97% cyclohexane, 16.27% cyclohexene and 81.76% benzene. % Conversion=18.24, % Selectivity=89.20. G.C. analysis of the recovered amine showed no evidence of any decomposition products.

EXAMPLE 7

A 35 mL heavy wall glass pressure tube was charged with Na/K alloy (206 mg), octamethyl pentaethylene hexamine (OMPEH) (329 mg. 0.956 mmol) and benzene (850 mg, 10.88 mmol) as in Example 1. A yellow color was produced after the colorless reactants had been stirred, under vacuum, at 25° C., for 20 minutes. The apparatus was then pressurized with 965 kPa $H_2$. There was no immediate color change. A yellow-green precipitate was produced after reacting for 16 hours. The volatile liquids were collected in an in-line trap (−196° C.) and analyzed by G.C. Found: 0.00% cyclohexane, 1.57% cyclohexene and 98.40% benzene. % Conversion=1.57, % Selectivity=100.00. G.C. analysis of the recovered amine showed little or no evidence of degradation.

EXAMPLE 8

A 35 mL heavy wall glass pressure tube was charged with iso-pentane/tetrahydrofuran- washed Na dispersion (212 mg), HMH (234 mg, 0.69 mmol) and benzene (794 mg, 10.17 mmol) as in Example 1. The reactants were stirred at 25° C. for 15 minutes. No blue color was observed. The apparatus was the pressurized with 1034 kPa $H_2$ and stirred at 25° C. for 1 hour. The gray slurry did not change color and most of the Na dispersion had coagulated into a large shiny lump. The pressure tube was immersed in liquid $N_2$ and the $H_2$ was pumped off. The benzene was distilled into a storage tube. The apparatus was taken into the drybox and charged with 16.72 mg Na/K alloy (78 wt. % K). It was then connected to the stainless steel pressure/vacuum line and the benzene from the storage tube was distilled back in. The mixture turned blue upon contact with the benzene. The color changed to green as soon as the apparatus was pressurized with 1034 kPa $H_2$. The reaction was run at 25° C., with stirring, under $H_2$ pressure for 40 hours. The $H_2$ was then pumped off and the volatile liquids were distilled into a collection tube and analyzed by G.C. Found: 0.02% cyclohexane, 16.89% cyclohexene and 83.07% benzene. % Conversion=16.91, % Selectivity=99.88. G.C. analysis of the recovered amine shows only a trace (0.03%) of HMH remaining. The solid hydride by-product was shown by x-ray powder analysis to be predominantly NaH.

EXAMPLE 9

A 35 mL heavy wall glass pressure tube was charged with 22/78 Na/K alloy (120 mg), HMH (300 mg, 0.88 mmol) and toluene (1300 mg, 14.1 mmol) as in Example 1. The mixture turned from blue to dark green upon contact with the toluene. The dark green mixture was stirred for 5 minutes at 25° C., after which time the apparatus was pressurized with 1000 kPa $H_2$. A dark green slurry was observed after reacting for 0.5 hours under the above conditions. A reaction time of 17 hours produced a yellow slurry. The $H_2$ was pumped off, the volatile liquids were distilled into a collection tube and analyzed by gas chromatography. Found: 0.19% 4-Methyl-cyclohexene, 2.25% 1-Methyl-1-cyclohexene and 97.33% toluene. Gas chromatography analysis of the contents of the pressure tube shows that almost all of the HMH had decomposed.

EXAMPLE 10

A 35 mL heavy wall glass pressure tube was charged with 22/78 Na/K alloy (139 mg), iso-HMTT (304 mg, 1.32 mmol) and toluene (850 mg, 9.23 mmol) as in Example 3. A pale yellow color was observed after the mixture had been stirred for 10 minutes at 25° C. The apparatus was then pressurized with 965 kPa $H_2$. The reaction mixture turned bright yellow upon the addition of $H_2$. Stirring under the above conditions for 20 minutes produced an orange color. Further reaction (16 hours total) gave a gray slurry. The reactor was then cooled to −196° C. and the $H_2$ was pumped off. The volatile liquids were collected in an in-line trap (−196° C.) and analysed by gas chromatography. Found: 1.85% 4-Methyl-1-cyclohexene, 2.00% 1-Methyl-1-cycohexene and 96.14% toluene. Gas chromatography analysis of the recovered amine shows no evidence of decomposition.

Examples 11 and 12 illustrate the purification of HMTT and iso-HMTT before their use in the earlier Examples.

EXAMPLE 11

An all-glass distillation apparatus was placed in an argon-filled drybox and to leg A was charged 2-3 grams Na/K alloy (78 wt. % K). The apparatus was then connected to an $N_2$ bubbler and 30 mL of HMTT was poured over the Na/K. This was stirred under $N_2$, for 16 hours, at 25° C. The apparatus was connected to a high vacuum line and evacuated. Leg A was immersed in a silicone oil bath and slowly heated to 100° C. while pumping under a dynamic vacuum ($10^{-5}$ torr). The first ¼ of the distillate was discarded. The heart cut was collected in leg B. The distilled HMTT was placed in a glass tube containing about 200 mg Na/K alloy, stirred overnight at room temperature and degassed. Gas chromatography analysis of the distilled HMTT shows a purity of >95%.

EXAMPLE 12

A glass distillation apparatus was charged with about 4 grams of Na/K alloy (78 wt. % K) and 30-35 mL iso-HMTT as described above. Leg A was heated to 65° C. under a dynamic vacuum ($10^{-5}$ torr) the first ¼ of the distillate was discarded. The fraction which distilled between 65°-75° C. was collected in leg B. The distilled iso-HMTT was placed in a glass tube containing about 200 mg Na/K alloy, stirred overnight at room temperature (25° C.) and degassed. Gas chromatography analysis shows the distilled product to be a mixture of 80% iso-HMTT and 14% HMTT.

What is claimed is:

1. A process for the selective hydrogenation of aromatic hydrocarbons which comprises reacting a liquid aromatic hydrocarbon selected from the group consisting of benzene and alkylbenzenes containing 7-10 carbons with an alkali metal selected from the group consisting of sodium, potassium and mixtures thereof, and with hydrogen in the presence of a polyamine containing only C, N and H, with at least 3 nitrogens, each nitrogen being linked to three carbons and each carbon bridge between nitrogens being at least two methylene units long, under conditions producing cyclohexene or alkylcyclohexene.

2. The method of claim 1 wherein said alkali metal is potassium.

3. The method of claim 1 wherein said alkali metal is a mixture of sodium and potassium.

4. The method of claim 1 or 2 or 3 wherein said aromatic hydrocarbon is benzene.

5. The method of claim 4 wherein said polyamine has at least 4 nitrogens, the carbon bridges between nitrogens are ethylene and the remaining alkyls are methyl or ethyl.

6. The method of claim 5 wherein said polyamine is

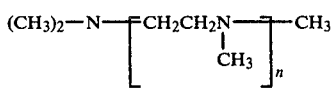

wherein n is an integer between 3 and 6, inclusive.

7. The method of claim 6 wherein n is 3.

8. The method of claim 5 wherein said polyamine is $N[CH_2CH_2N(CH_3)_2]_3$.

9. The method of claim 5 wherein said polyamine is a cyclic amine of the formula:

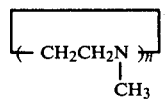

wherein n is an integer between 5 and 8, inclusive.

10. The method of claim 9 wherein n is 6.

* * * * *